(12) United States Patent
Li et al.

(10) Patent No.: US 10,905,538 B2
(45) Date of Patent: Feb. 2, 2021

(54) LUNG-VOLUME-REDUCTION ELASTIC IMPLANT AND LUNG-VOLUME REDUCTION INSTRUMENT

(71) Applicant: Lifetech Scientific (Shenzhen) Co., Ltd., Shenzhen (CN)

(72) Inventors: Anning Li, Shenzhen (CN); Siyi Li, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 100 days.

(21) Appl. No.: 15/767,614

(22) PCT Filed: Jun. 29, 2016

(86) PCT No.: PCT/CN2016/087721
§ 371 (c)(1),
(2) Date: Apr. 11, 2018

(87) PCT Pub. No.: WO2017/063383
PCT Pub. Date: Apr. 20, 2017

(65) Prior Publication Data
US 2018/0303593 A1    Oct. 25, 2018

(30) Foreign Application Priority Data

Oct. 15, 2015  (CN) .......................... 2015 1 0675725

(51) Int. Cl.
*A61F 2/04*     (2013.01)
*A61B 17/12*    (2006.01)
(Continued)

(52) U.S. Cl.
CPC .......... *A61F 2/04* (2013.01); *A61B 17/12104* (2013.01); *A61B 17/12145* (2013.01);
(Continued)

(58) Field of Classification Search
CPC .................................... A61F 2/06; A61F 2/36
See application file for complete search history.

(56) References Cited

U.S. PATENT DOCUMENTS

| 5,108,368 A * | 4/1992 | Hammerslag ..... A61M 25/0144 600/585 |
| 9,402,633 B2 * | 8/2016 | Vasquez .......... A61B 17/12104 |

FOREIGN PATENT DOCUMENTS

| CN | 102209570 A | 10/2011 |
| CN | 10380299 A | 6/2014 |

(Continued)

*Primary Examiner* — Yashita Sharma
(74) *Attorney, Agent, or Firm* — Raymond Sun

(57) ABSTRACT

A lung-volume-reduction elastic implant (500) is tubular and at least the proximal end of the implant has an opening. The implant (500) comprises an elastic deforming part (51) and a flexible guiding part (53) connected to the distal end of the elastic deforming part (51). The elastic deforming part (51) has a shape memory property. The elastic deforming part (51) is provided in the lengthwise direction thereof with several slots (514) at intervals, wherein each slot (514) communicates with the tubular cavity of the elastic deforming part (51). Under the same externally applied force, the flexible guiding part (53) deforms more easily than the elastic deforming part (51). An implant delivering instrument (600) comprises an implant (500) and a matching delivering means (700). The delivering means (700) comprises a core wire (71) and a hollow pushing member (73). The implant (500) is detachably connected to the distal end of the pushing member (73) by means of the proximal end of the implant. The core wire (71) movably passes through the tubular cavity of the implant (500) and the tubular cavity of the pushing member (73).

16 Claims, 12 Drawing Sheets

(51) Int. Cl.
 *A61B 17/00* (2006.01)
 *A61B 1/012* (2006.01)
 *A61B 1/267* (2006.01)
 *A61B 5/08* (2006.01)

(52) U.S. Cl.
 CPC ............. *A61B 1/012* (2013.01); *A61B 1/2676* (2013.01); *A61B 5/08* (2013.01); *A61B 2017/00526* (2013.01); *A61B 2017/00867* (2013.01); *A61B 2017/1205* (2013.01); *A61F 2002/043* (2013.01)

(56) References Cited

FOREIGN PATENT DOCUMENTS

| | | |
|---|---|---|
| CN | 105455930 A | 4/2016 |
| JP | 2013223589 A | 10/2013 |

* cited by examiner

LUNG-VOLUME-REDUCTION ELASTIC IMPLANT AND LUNG-VOLUME REDUCTION INSTRUMENT

TECHNICAL FIELD

The present disclosure belongs to the technical field of interventional therapy, relates to an implant and a device for the interventional therapy, and particularly relates to a lung volume reduction elastic implant and a lung volume reduction device.

BACKGROUND ART

Pulmonary emphysema is a common pulmonary disease. Traditional internal therapies for pulmonary emphysema include oxygen inhalation, pulmonary infection prevention, bronchus spasm relaxation and the like, but the curative effect is extremely limited. Surgical therapies for pulmonary emphysema mostly adorning volume reduction surgery, and there are also many limitations: for example: strict surgical indications, risks of many complications, anesthesia and anesthesia-related complications, difficulty in predicting the curative effect before the surgery, and an irreparable non-ideal curative effect caused by over-cutting or sub-cutting matter the surgery, excessively high surgery cost, and great mental and physical sufferings. In addition, some patients cannot always tolerate the surgery due to their poor lung functions, and this leads to a higher postoperative mortality rate, which limits the use of surgical operation.

In order to better treat pulmonary emphysema, improve quality of life of a patient, and reduce traumas to the patient during surgery, internationally, it has been researched to use a bronchoscope to implement interventional modes such as one-way valve, biogel, steam thermal ablation and elastic coil for treating pulmonary emphysema. However, the one-way valve has been rejected by the FDA (Food and Drug Administration) in the USA due to its low clinical indicators that residual gas and sputum in a target region cannot be effectively and actively excreted, and technical difficulties in collateral ventilation and precise placement of the one-way valve at different anatomical structural positions also limit the curative effectiveness of the one-way valve. The problem that the biogel completely blocks an emphysema region and leads to postoperative inflammation is still unsolved. Steam thermal ablation would lead to the postoperative inflammation due to a defect of destroying an original tissue structure of the emphysema region.

At the present, an updated therapy method is adopted for pulmonary emphysema, meaning that an elastic coil serving as an implant is implanted into a lesion portion of the lung of a human body. FIG. 1 is a schematic diagram of a lung volume reduction elastic coil in the prior art. This product is designed and made of a nickel-titanium memory alloy metal wire, and may elastically deform under the action of an external force. Under the restriction of a loading system, this product may be implanted into the lung through a working channel of a bronchoscope in a straight line form. After being delivered into a bronchus of a pulmonary emphysema region, the coil is released from the restriction of the loading system and then recovers to its natural shape (which is a shape without the external force) as shown in FIG. 1, and at the same time, the pulmonary emphysema region is squeezed under the pulling action of the nickel-titanium alloy wire, thereby discharging gas in the bronchus and reducing the volume of a lung tissue in the pulmonary emphysema region; and therefore, a relatively healthy lung tissue therearound may provide better physiological function.

A surgical method using the elastic coil includes three operation processes of inserting a bronchoscope, building a channel, and then implanting a product. Insertion of the bronchoscope is as shown in FIG. 2: a bronchoscope 201 is inserted through a mouth or a nose, and may display an image detected by the distal end 203 of the bronchoscope 201 on a monitor 204, thereby guiding the bronchoscope 201 to reach the bronchus 205 of a human lung.

Building of the channel is as shown in FIG. 2. The outer diameter of a guide wire 206 is about 5 Fr to 7 Fr, and the diameter of a delivery sheath may be about 5 Fr to 9 Fr. The guide wire 206 is moved to pass through an inner cavity of an expander 207, and the expander 207 is moved to pass through an inner cavity of the delivery sheath 208; after being assembled, the guide wire 206, the expander 207 and the delivery sheath 208 enter the bronchoscope 201 together from a working channel 202 of the bronchoscope 201, and then pass through the distal end 203 of the bronchoscope 201 and enter the bronchus 205. A length label 210 is disposed at the distal end 209 of the guide wire 206, and indicates a distance along the guide wire 206 from the distal end 209. The distal end 211 of the delivery sheath 208 may have multiple corresponding labels 210 in a form of high-contrast metal straps (including gold, platinum, tantalum, iridium, tungsten and/or metalloids). A fluorescence inspection system, an ultrasonic imaging system, an MRI (Magnetic Resonance Imaging) system, an X-ray CT (Computerized Tomography) system, which are provided with a remote imaging and capturing device 212, or some other remote imaging implants, are configured to guide the guide wire 206. As shown in FIG. 2, the remote imaging and capturing device 212 may display a detected image on a monitor 213, and identify a track of the guide wire 206 or an imaging label 210, thereby building the channel.

After the channel is built, the expander 207 and the guide wire 206 are pulled out towards the proximal end from the delivery sheath 208, so that a lung volume reduction elastic coil 301 may be loaded in an open cavity of the delivery sheath 208. Implantation of the coil 301 is shown in FIG. 3, and the loading system 302 with the coil 301 is connected to the proximal end of the delivery sheath 208 through a locking hub connector 303. The coil 301 is introduced into the delivery sheath, as shown in FIG. 4, and a steel cable 305 of an actuation device 304 pushes the product out of the distal end of the delivery sheath 208 and enables the product to enter the bronchus 205. And then the delivery sheath 208 is withdrawn, and a gripper 306 of the actuation device 304 is configured to release the coil 301. When recovering to its initial shape, the coil 301 also pulls the bronchus 205 to be in a curled shape, thereby achieving pulmonary emphysema volume reduction.

The above-mentioned implant and its implantation method have the following defects:

1. An elastic coil is required to be released through the delivery sheath, which may injure the inner wall of a bronchus during its pushing in the bronchus and cause adverse events such as pneumothorax.

2. As the delivery sheath has a relatively large outer diameter of about 5 Fr to 9 Fr, it is really hard to implant the elastic coil into a lung bypass or the ends of some small-diameter tracheas, and only a limited pulmonary emphysema region is squeezed and pulled by the elastic coil, thus affecting the effects of the volume reduction.

3. The existing surgical method for implanting an elastic coil needs three independent operation processes of inserting the bronchoscope, building the channel, and implanting the product, so that a relatively long operation time is needed. In addition, as the surgery is conducted when a patient is awake, extremely long operation time may easily lead to adverse events such as discomfort of the patient, and acute exacerbation of a COPD (Chronic Obstructive Pulmonary Disease).

SUMMARY OF THE INVENTION

In order to solve the technical problems, in view of the above-mentioned defects in the prior art, the present disclosure provides an implant which is directly delivered through a core wire instead of a delivery sheath. The adoption of the implant may prevent the delivery sheath from injuring the inner wall of a bronchus, and reduce the incidence of pneumothorax.

In order to further solve the technical problems, the present disclosure provides a lung volume reduction device which may implant the implant into a lung bypass or the ends of some small-diameter tracheas according to an actual requirement, integrate a channel building process with an implant implantation operation process, make surgical operation more convenient, shorten the surgical operation time, and achieve a better treatment effect.

A technical scheme adopted by the present disclosure to solve the technical problems is as follows:

A lung volume reduction elastic implant is provided, which is tubular and which is open at the proximal end. The implant includes an elastic deformation section and a flexible guide section connected with the distal end of the elastic deformation section. The elastic deformation section has a shape memory characteristic and has a plurality of grooves formed in a spaced-apart manner along its lengthwise direction. Each groove communicates with the lumen of the elastic deformation section. Under the action of the same external force, the flexible guide section deforms more easily than the elastic deformation section.

In one embodiment of the technical scheme, on an unfolded plane formed by splitting the elastic deformation section along its axial direction, an included angle between the incision direction of each groove and the lengthwise direction of the elastic deformation section ranges from 10 to 90 degrees; and the shapes and the arrangement of the grooves meet requirements of the elastic deformation section on bending and twisting in multiple directions and meet a bending resistance requirement of the implant.

The elastic deformation section is made of a conical nickel-titanium tube having an outer diameter gradually increased from the distal end to the proximal end, and a gap of 0.05 mm to 0.5 mm is formed between every two adjacent grooves of the elastic deformation section.

In one embodiment of the technical scheme, the implant timber includes an elastic film that at least wraps around the outer wall of the elastic deformation section and the flexible guide section.

In one embodiment of the technical scheme, the grooves are further filled with the elastic film.

In one embodiment of the technical scheme, the bending resistance of the flexible guide section is gradually enhanced from the distal end to the proximal end.

In one embodiment of the technical scheme, the flexible guide section includes a main body portion having a spring on the outer wall; the proximal end of the main body portion is connected with the elastic deformation section; and the outer diameter of the main body portion is gradually increased from its distal end to proximal end.

In one embodiment of the technical scheme, the flexible guide section includes a tubular body which is cut from a nickel-titanium tube and has continuous spiral grooves.

In one embodiment of the technical scheme, on an unfolded plane formed by splitting the flexible guide section along its axial direction, the gap between every two adjacent grooves of the flexible guide section along the axial direction of the flexible guide section is gradually increased from the distal end to the proximal end of the flexible guide section.

In one embodiment of the technical scheme, on the unfolded plane formed by splitting the flexible guide section along its axial direction, from the distal end to the proximal end of the flexible guide section, an acute angle between the extending direction of the grooves of the flexible guide section and the axial direction of the flexible guide section is unchanged, and the widths of the grooves of the flexible guide section along the axial direction of the flexible guide section are gradually decreased.

In one embodiment of the technical scheme, on the unfolded plane formed by splitting the flexible guide section along its axial direction, from the distal end to the proximal end of the flexible guide section, the widths of the grooves of the flexible guide section along the axial direction of the flexible guide section are unchanged, and an acute angle between the extending direction of the grooves of the flexible guide section and the axial direction of the flexible guide section is gradually decreased.

In one embodiment of the technical scheme, the distal end of the flexible guide section extends outwardly and is connected with a flexible guide section end head, and an imaging label is disposed on the flexible guide section end head.

In one embodiment of the technical scheme, the flexible guide section end head closes the distal end of the flexible guide section.

In one embodiment of the technical scheme, an included angle between the axial line of the distal end of the flexible guide section and the axial line of the distal end of the elastic deformation section ranges from 5 to 60 degrees.

In one embodiment of the technical scheme, a connection member is disposed at the proximal end of the implant.

A lung volume reduction device is provided, including any one of the above-mentioned implants and a delivery device for use with the implant. The delivery device includes a core wire and a hollow pushing member; the implant is detachably connected to the distal end of the pushing member through its proximal end; the core wire may be movably disposed in, and extends through, a lumen of the implant and a lumen of the pushing member.

In one embodiment of the technical scheme, a core wire guide head coaxial with the core wire is disposed at the distal end of the core wire, and the outer diameter of the core wire guide head is consistent with that of the core wire.

In one embodiment of the technical scheme, the core wire guide head includes a guide post and a spring disposed on the guide post in a sleeved manner; the guide post and the core wire are made in an integral structure, or the guide post is fixedly connected to the distal end of the core wire; and the spring has an imaging label.

Compared with the prior art, an implant of the present disclosure is tubular and is at least opened at its proximal end, and the core wire may be directly inserted into the lumen of the implant to restrict the implant in a straight line form for delivery; so that no delivery sheath with a larger outer diameter than the implant is required for restricting the implant, thereby preventing the delivery sheath from injuring the trachea in a delivery process and further reducing the incidence of pneumothorax.

An implant of the present disclosure has a hollow lumen structure, so that the core wire is conveniently inserted through the lumen of the implant in advance during operation to enable the implant to be disposed on the core wire, and then the implant and the core wire are pushed into the bronchus in a pulmonary emphysema region together through the bronchoscope. As previously mentioned, the core wire or the implant builds the channel by itself; after the implant is pushed to a proper target region, the core wire would be withdrawn to release the implant, thus the two operation processes of building the channel and implanting the implant in the prior art are completed synchronously, which may effectively shorten the surgical operation time to avoid adverse events such as acute exacerbation of a COPD (Chronic Obstructive Pulmonary Disease).

Further, the surface of an elastic deformation section of the implant or the surface of the whole implant is wrapped by one elastic film, so as to avoid direct contact between a metal surface of an implant and the inner wall of the bronchus, thereby reducing the release of metal elements and effectively reducing pneumonia or small airway infections.

According to the lung volume reduction device of the present disclosure, a core wire is configured to load an implant, guide the building of the channel, deliver the implant and release it; or a guide head is disposed at the distal end of the implant, also plays a role in guiding and building a channel, and may release the implant immediately after the channel is built; and this scheme is configured to integrate the channel building process with the implant implantation operation process, so that the surgical operation is more convenient, and the surgical operation time is further shortened.

According to the lung volume reduction device of the present disclosure, a delivery device inserts core wire through an implant having a lumen structure, and completes delivery of the implant through pushing of a pushing mechanism. Under the restriction of a core wire, an implant turns into a delivers state (namely a straight line form matched with the shape of a core wire) from a natural state (namely a preset curled state obtained by thermal treatment); after the core wire is withdrawn from the lumen of an implant, the restriction of the core wire is relieved, so that the implant may return to the natural state from the delivery state, achieving an effect of squeezing a target pulmonary emphysema region. Compared with a delivery, sheath in the prior art, the delivery device has no delivery sheaths, so that the diameter is smaller, and the implant may enter a smaller target pulmonary emphysema region to achieve a better treatment effect. By adoption of the technical scheme of combining channel building and implant releasing, the present disclosure may shorten the whole surgical time, and may be located in the target pulmonary emphysema region more precisely.

According to the lung volume reduction device of the present disclosure, the surface of an implant is further surrounded by one elastic film which is made of a macromolecular material having a higher biocompatibility, so that the elastic film made of the macromolecular material is in contact with the inner wall of the bronchus. Compared with the prior art scheme where a nickel-titanium wire is in direct contact with the inner wall of the bronchus, a lung volume reduction device of the present disclosure may reduce bronchial inflammation and injury caused by friction between the implant and the inner wall of the bronchus in a respiration process, thereby reducing risks of pneumonia and small airway infections. In addition, wrapping the metal surface of the implant with the elastic film made of the macromolecular material may effectively reduce release of metal elements.

BRIEF DESCRIPTION OF THE DRAWINGS

A further description for the present disclosure in combination with accompanying drawings and embodiments is as follows. In the drawings.

DETAILED DESCRIPTION OF THE INVENTION

For the purpose of making the objects, features and advantages of the present disclosure more clear, a detailed description for specific implementation modes of the present disclosure in conjunction with accompanying drawings is as follows. Many specific details are specified in descriptions as follows to facilitate full understandings of the present disclosure. However, the present disclosure may be implemented through many other modes different from those described herein. A person skilled in the art can make similar improvements without departing from contents of the present disclosure, thus the present disclosure should not be limited by the specific embodiments disclosed as follows.

In the field of interventional medicine, generally, an end relatively close operator is called a proximal end, and an end relatively far away from the operator is called a distal end.

Unless otherwise defined, all technical and scientific terms used herein have the same meanings of general understandings of persons skilled in the art of the present disclosure. Terms used in the description of the present disclosure herein are only intended to describe the specific embodiments, but not to limit the present disclosure. Terms "and/or" used herein include any and all combinations of one or multiple relevant listed items.

Figure 1:
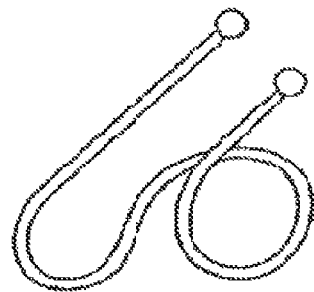
FIG. 1 is a structural schematic diagram of an elastic coil in the prior art.
Figure 2:
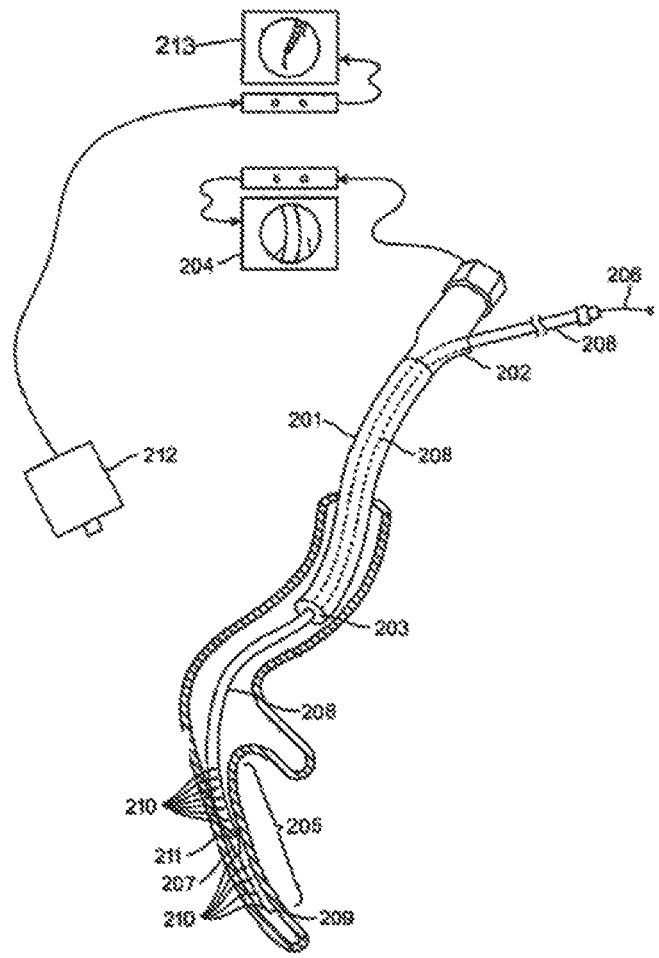
FIG. 2 is an operation schematic diagram of the implantation of a bronchoscope and the building of a channel through a core wire in a prior art.
Figure 3:
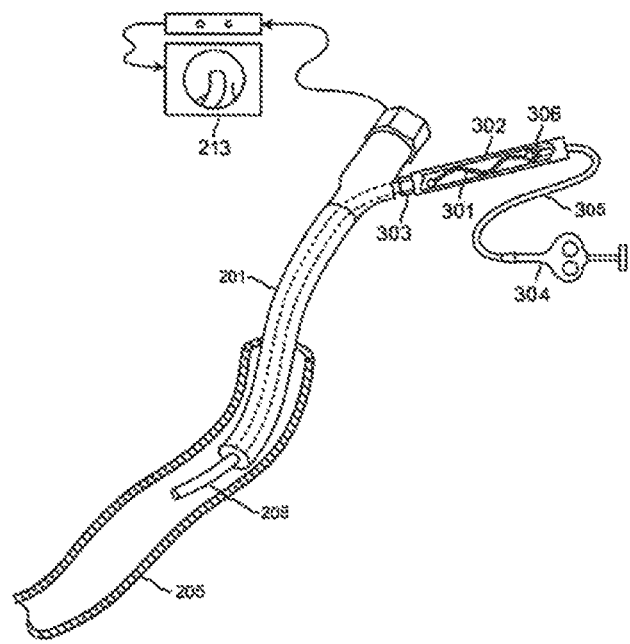
FIG. 3 is a schematic diagram of the delivery of an elastic coil in a prior art.
Figure 4:
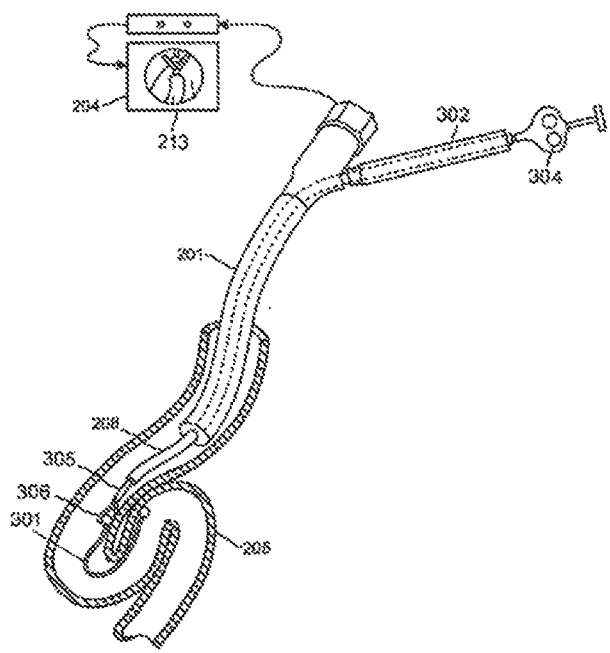
FIG. 4 is a schematic diagram of the release of an elastic coil in a prior art.
Figure 5:
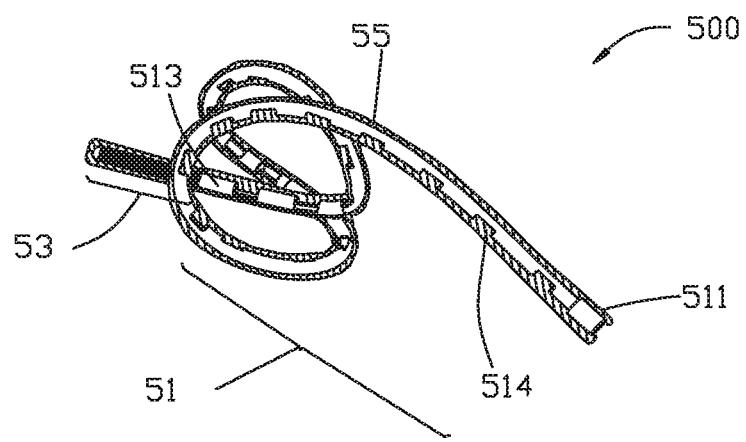
FIG. 5 is a schematic diagram of an implant, on which part of a film is torn away, provided by one embodiment of the present disclosure.

With reference to FIG. 5, an elastic implant 500 provided by one embodiment of the present disclosure is of a tubular structure, which includes a hollow tubular elastic deformation section 51, a flexible guide section 53 connected with the elastic deformation section 51, and an elastic film 55 disposed on the elastic deformation section 51 and the guide section 53. The implant 500 has an open proximal end; the elastic deformation section 51 and the guide section 53 may be of an integrated structure, or are fixedly connected with each other. The distal end of the flexible guide section 53 is the distal end of the elastic implant 500. Under the action of the same external force, the flexible guide section 53 deforms more easily than the elastic deformation section 51 (that is to say, under the action of the same external force, the bending resistance of the flexible guide section 53 is lower than that of the elastic deformation section 51), so that it may move better in a bronchus without injuring a surrounding tissue.

The elastic deformation section 51 has a shape memory characteristic, and includes a proximal end 511 and a distal end 513 which are opposite each other; and the distal end 513 is connected with the flexible guide section 53. The elastic deformation section 51 further includes multiple grooves 514 which are isolated from one another and are communicated with a lumen of the elastic deformation section 51. The multiple grooves 514 enable the elastic deformation section 51 of the elastic implant 500 to be bent into a preset shape in a natural state, for example, a shape as shown in FIG. 5.

In the natural state (namely without any external force), the elastic deformation section 51 is of a preset curled shape, but under the action of an external force, it may be restricted into a straight line form or any other shapes, and would be recovered into the preset shape through bending and twisting if the external force is withdrawn. The elastic deformation section 51 may be made of any material which is commonly used in this industry and has shape memory function. The present disclosure does not limit specific materials, and materials which are applicable to human body and have the shape memory function are acceptable. In this embodiment, the elastic deformation section 51 is made of a nickel-titanium alloy. To be more specific, a machining method of an elastic deformation section 51 includes: first, cutting a section of hollow nickel-titanium tube having a diameter of about 0.5 to 2.0 mm and a wall thickness of 0.01 to 0.4 mm with laser; then bending the cut nickel-titanium tube with a die into a shape of an elastic deformation section 51 as shown in FIG. 5; and finally, performing thermal treatment for modeling, thus obtaining the elastic deformation section 51.

Figure 6:
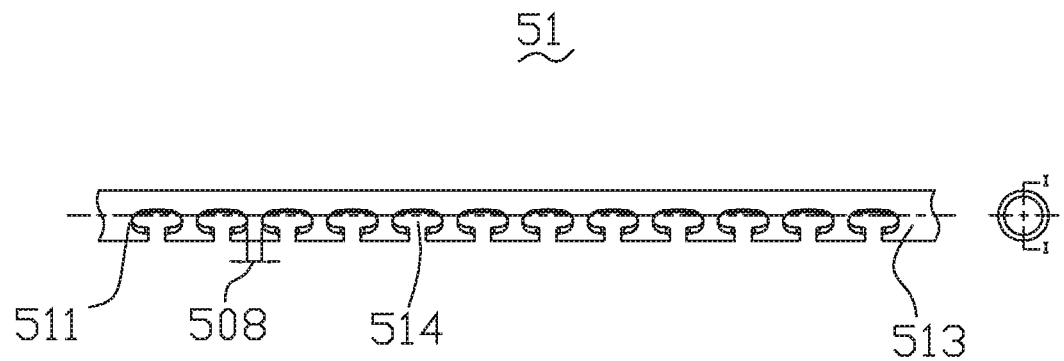
FIG. 6 is a sectional view of an elastic deformation section of the implant as shown in FIG. 5.
Figure 7:
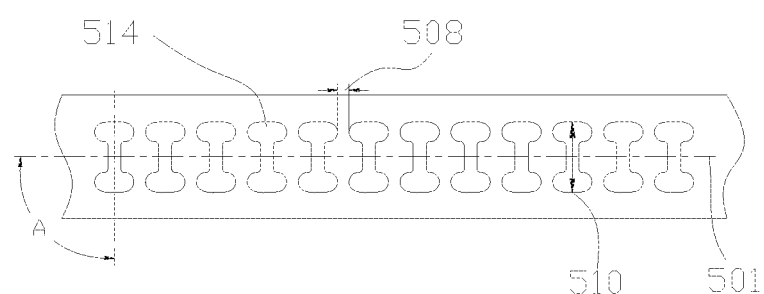
FIG. 7 is a schematic diagram of a groove obtained by splitting and unfolding the elastic deformation section of the implant in FIG. 5 along its lengthwise direction.

Referring together to FIG. 6 and FIG. 7, in this embodiment, so that the elastic deformation section 51 may extend into a thinner bronchus to achieve a better squeezing effect on a corresponding tissue, preferably, the elastic deformation section 51 is made of a conical nickel-titanium tube having a consistent inner diameter and a gradually varying wall thickness, for example, a conical nickel-titanium tube having an inner diameter of 0.8 to 1.0 mm and a wall thickness varying from 0.01 mm at the distal end to 0.4 mm at the proximal end; multiple dumbbell-shaped grooves 514 are formed in the nickel-titanium tube, and an extending direction 510 (namely an incision direction) of these grooves 514 and the axial line 501 of the elastic deformation section 51 form a certain angle A which is preferably 10 to 90 degrees. A gap 508 of about 0.05 mm to 0.5 mm is formed between every two adjacent grooves 514. It should be understood that as the elastic deformation section 51 has the multiple grooves 514, its bending resistance may vary, with changes of the lengths of the grooves 514 along their extending direction 510. A person skilled in the art could set the lengths of the grooves 514 of the elastic deformation section 51 in their extending direction 510 according to an actual requirement to achieve an objective that the bending resistance of the flexible guide section 53 is lower than that of the elastic deformation section 51.

Figure 8:
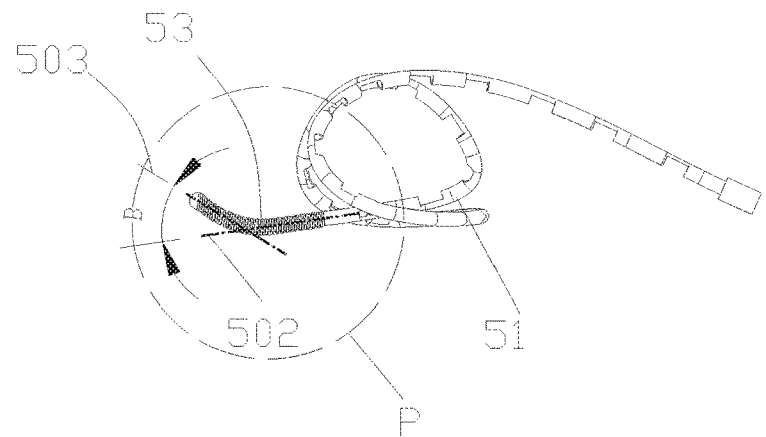
FIG. 8 is a schematic diagram of the implant without a film in FIG. 5.
Figure 9:
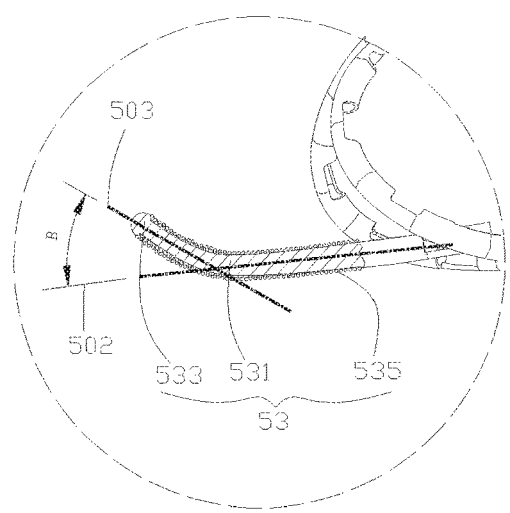
FIG. 9 is an enlarged view of a portion P in FIG. 8.

Referring together to FIG. 8 and FIG. 9, the flexible guide section 53 is disposed at the distal end of the elastic deformation section 51, and is configured to play a guide role for the elastic deformation section 51. The axial line 503 at the distal end of the flexible guide section 53 and the axial line 502 at the distal end 511 of the elastic deformation section 51 form an included angle B which may be 5 to 60 degrees. In this embodiment, the flexible guide section 53 includes a main body portion 531, a flexible guide section head end 533 disposed at the distal end of the main body portion 531 and a spring 535 disposed on the outer wall of the main body portion 531.

The main body portion 531 may support the spring 535, and may be made of a metal with relatively high elasticity, such as a nickel-titanium alloy and a cobalt-chromium alloy, and the outer diameter of the main body portion 531 is gradually increased from the distal end of the main body portion 531 to the proximal end of the main body portion 531. The proximal end of the main body portion 531 is connected with the distal end 511 of the elastic deformation section 51 through the use of macromolecular heat-shrink tube or film wrapping, glue adhesion, laser welding, soldering and the like. In this embodiment, the main body portion 531 is a solid nickel-titanium rod. It should be understood that the main body portion 531 also may be a hollow nickel-titanium tube. As a hollow nickel-titanium tube, if the inner diameter of the main body portion 531 does not change from the proximal end to the distal end, its outer diameter is gradually increased from the distal end to the proximal end, and if the outer diameter of the main body portion 531 does not change from the proximal end to the distal end, its inner diameter is gradually decreased from the distal end to the proximal end.

In this embodiment, the distal end of the spring 535 and the distal end of the main body portion 531 are fused together at high temperature, thus forming the flexible guide section head end 533. The flexible guide section head end 533 is coaxial with the distal end of the main body portion 531 and closes the distal end of the main body portion 531. The flexible guide section head end 533 may further have an imaging label (not shown in the figures).

The spring 535 is formed by winding a metal wire with a diameter of 0.05 to 0.5 mm (preferably, a tungsten metal wire, a tantalum metal wire and the like with relatively high X-ray developing property). It should be understood that the flexible guide section head end 533, the spring 535 and the main body portion 531 may be formed separately as well, and then the flexible guide section head end 533, and the distal end of the spring 535 are connected together with the distal end of the main body portion 531 through the use of macromolecular heat-shrink tube or film wrapping, glue adhesion, laser welding and the like; in case of separate forming, preferably, the flexible guide section head end 533 is made of a metal with relatively high X-ray developing property, such as tungsten and tantalum. It should also be understood that the flexible guide section head end 533 may be removed as required.

In addition, it should be understood that if there is no flexible guide section head end 533, and the main body portion 531 is the hollow nickel-titanium tube, on one hand, a closing member made of the same material or a similar material as the guide head 533 may be disposed in the proximal end of the main body portion 531 to fully close or partially-close the distal end of the elastic deformation section 51. On the other hand, the proximal end of the main body portion 531 may also be communicated with the elastic deformation section 51; and at this moment, the implant 500 is opened at both the proximal end and the distal end. In any case, it is only necessary to ensure that a core wire (specifically described below) does not penetrate through the distal end of the flexible guide section 53; that is to say, when the implant 500 opens at the distal end, it is necessary to ensure that the core wire may enter the implant 500 and that the outer diameter of the core wire would be larger than that of an in-circle of the opening at the distal end of the implant 500 (i.e., when the opening is a non-circular opening, such as a triangular opening and a square opening) or larger than that of the opening in the distal end (when the opening is a circular opening).

Figure 10:
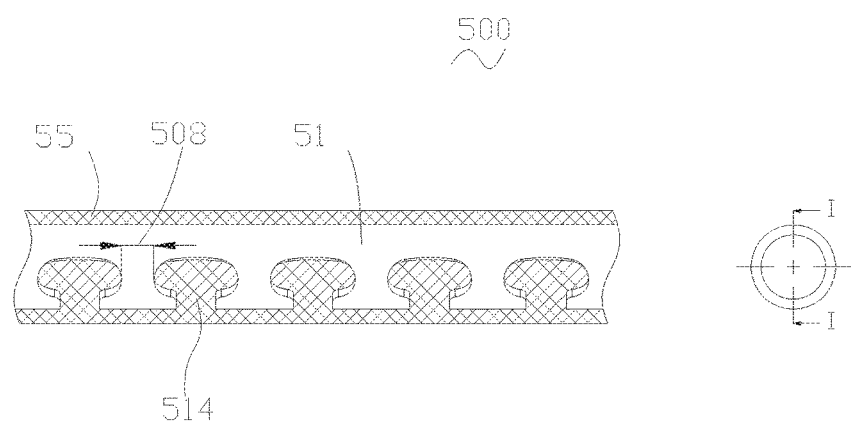
FIG. 10 is a sectional view of part of the implant in FIG. 5.

Referring, together to FIG. 5 and FIG. 10, the elastic implant film 55 completely wraps the outer surface of the elastic implant 500, and each groove 514 is filled with the film, but the film does not block the lumen of the elastic implant 500, thereby ensuring that the elastic implant film 55 firmly wraps the elastic implant 500 and also ensuring that the lumen of the elastic implant 500 is unblocked. The elastic implant film 55 may have a thickness of 0.01 mm to 0.8 mm, and may be prepared from macromolecular solutions featuring high chemical stability, water resistance and weather aging resistance, good low compressibility, good biocompatibility, high mechanical strength, non-toxicity, odorlessness and the like. For example, these macromolecular solutions may be silicone rubber or polyurethane solutions.

Figure 11:
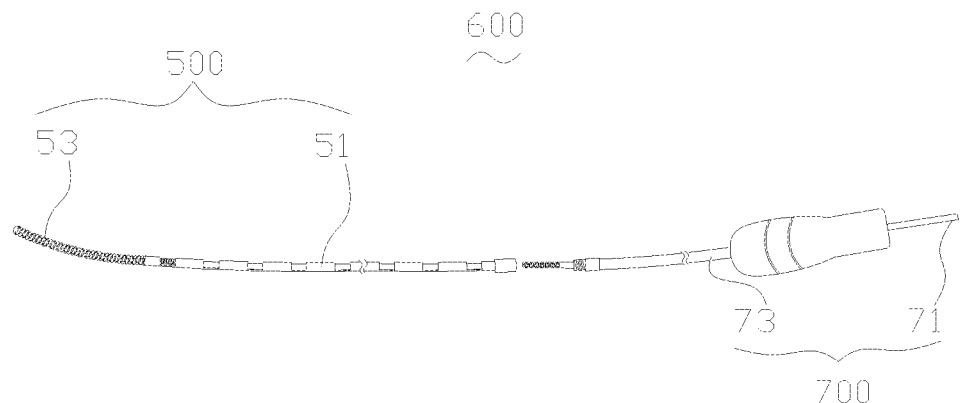
FIG. 11 is a schematic diagram of a lung volume reduction device provided by one embodiment of the present disclosure.

With reference to FIG. 11, a lung volume reduction device 600 provided by one embodiment of the present disclosure includes an elastic implant 500 and a delivery device 700. The delivery device 700 includes a core wire 71 and a pushing mechanism 73.

The core wire 71 is accommodated in the lumen of an elastic implant 500, and is configured to limit the elastic implant 500 in an approximately straight line tope delivery state to facilitate delivery of the implant 500 to a lesion portion; thus no delivery sheath is needed to restrict the implant 500, which prevents having a delivery sheath injuring a trachea in a delivery process and further reduces the incidence of pneumothorax. The core wire 71 may be made of a section of a metal wire having a diameter of 0.1 mm to 1.1 mm. Compared with the prior art, the present disclosure does not require any delivery sheath, so that the implant 500 may be implanted into a lung bypass or the ends of some small-diameter tracheas to achieve a better treatment effect.

Figure 12:
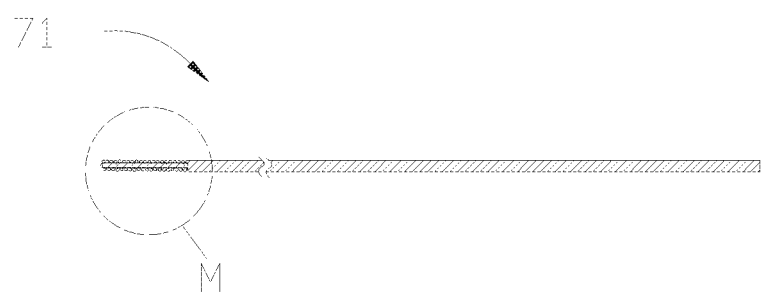
FIG. 12 is a schematic diagram of a core wire of the lung volume reduction device in FIG. 11.
Figure 13:
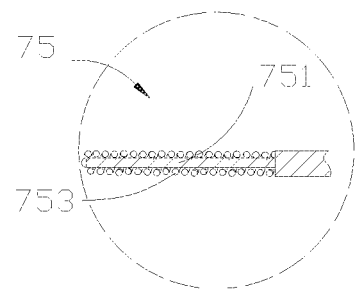
FIG. 13 is an enlarged view of a portion M in FIG. 12.

Referring together to FIG. 12 and FIG. 13, for the purpose of safety and convenience in operation, it is necessary to dispose a flexible core wire guide head 75, which is coaxial with the core wire 71 and has an imaging label, at the distal end of the core wire 71. The outer diameter of the core wire guide head 75 is consistent with that of the core wire 71. The core wire guide head 75 includes a guide post 751 and a spring 753 fixed outside, and surrounding, the guide post 751. The guide post 751 and the core wire 71 can be of an integrated structure, or the guide post 751 is fixedly connected to the distal end of the core wire 71; and the spring 753 has an imaging label.

Figure 17:
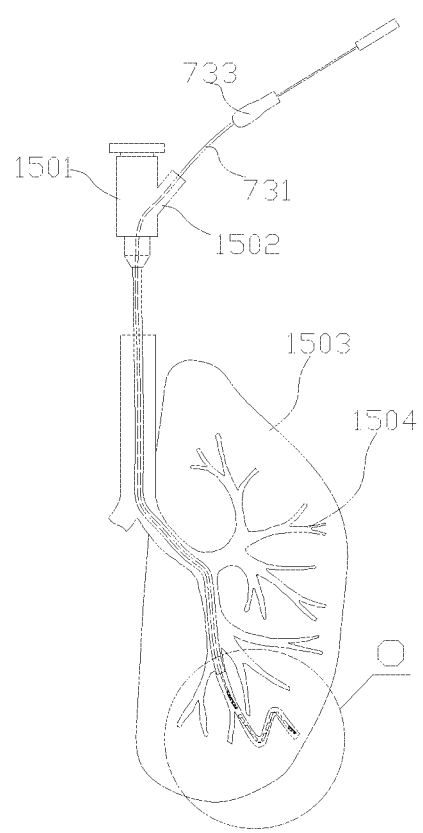
FIG. 17 is a schematic diagram of an implant released.
Figure 18:
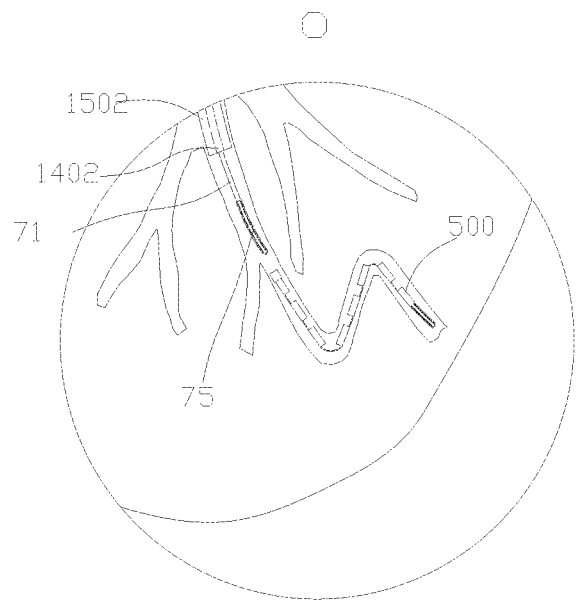
FIG. 18 is an enlarged view of a portion O in FIG. 17.

The core wire guide head 75 is configured to guide the core wire 71 to successfully enter the lumen of the elastic implant 500. The flexible core wire guide head 75 may be implemented through a flexible spring, and namely the spring 753 surrounds the guide post 751 which is of an integrated structure with the core wire 71, or is fixedly connected to the distal end of the core wire 71. A specific manufacturing method may include; first thinning the head end of the core wire 71 to manufacture the guide post 751, and then fixing a section of the spring 753 having a length of 5 mm to 150 mm outside the guide post 751. The spring 753 and the core wire 71 may be fixed via a macromolecular heat-shrink tube or film wrapping, glue adhesion, laser welding, soldering and the like. Under the guidance of the flexible core wire guide head 75, the core wire 71 may successfully enter the lumen of the implant 500 from the proximal end of the implant 500 to restrict the implant 500 into an approximate straight line form (as shown in FIG. 17) from the shape as shown in FIG. 5 and FIG. 8.

In this embodiment, with the flexible guide section 53, the implant 500 equipped with a core wire 71 further has a function of exploring a path in the bronchus to reach the lesion region. It is necessary to dispose the imaging label on the core wire guide head 75 to guide and monitor an operation condition of the core wire 71 in the lung. The imaging label can display the implant through the use of a fluorescence inspection system, an ultrasonic imaging system, an MRI (Magnetic Resonance Imaging) system, an X-ray CT (Computerized Tomography) system or other remote imaging, and there is no limitation to any specific structure. The core wire 71 is developed and guided through these systems. In this embodiment, the spring formed by winding a metal wire with the diameter of 0.01 to 0.3 mm and relatively high X-ray developing property, such as a tungsten metal wire and a tantalum metal wire, is used as the imaging label. In this embodiment, the imaging label and the core wire guide head 75 are combined into one component to realize two functions. Besides such a mode, an extra imaging label may be disposed on the core wire guide head 75. Of course, when the surface of the implant of the present disclosure is not wrapped by an elastic film, and the implant is made of a material capable of realizing X-ray developing by itself, such as the nickel-titanium alloy, no imaging label is provided.

Figure 14:
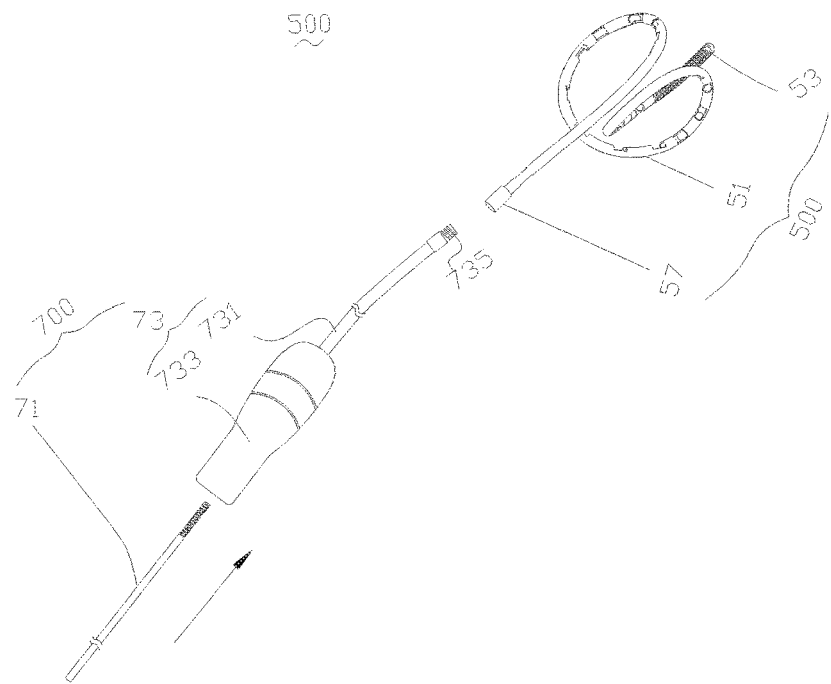
FIG. 14 is a schematic diagram showing assembling of the lung volume reduction device in FIG. 11.
Figure 15:
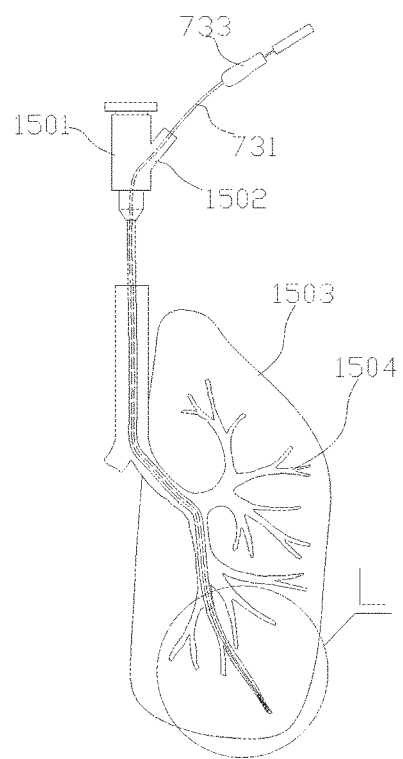
FIG. 15 is a schematic diagram showing the building of a working channel of a lung volume reduction device provided by one embodiment of the present disclosure.
Figure 16:
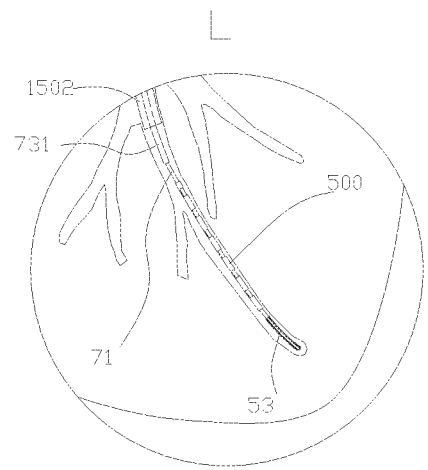
FIG. 16 is an enlarged view of a portion L in FIG. 15.

Referring also to FIG. 14, the pushing mechanism 73 includes a hollow pushing member 731 and a control handle 733 connected with the hollow pushing member 731. The hollow pushing member 731 and the implant 500 are disposed on the core wire 71 in a sleeved manner in sequence from outside to inside; and the distal end of the hollow pushing member 731 is detachably connected with the proximal end 511 of the implant 500. In this embodiment, a connection member 57 having an internal thread (not shown in the Figure) is welded at the proximal end of the implant 500; and the hollow pushing member 731 is a pushing steel cable, and a connection matching member 735 having an external thread matching with the internal thread of the connection member 57 is disposed at the distal end of the hollow pushing member 731. In other implementation modes, an internal thread serving as the connection member 57 also may be directly turned at the proximal end of the implant 500.

During assembly, the internal thread of the connection member 57 is in threaded connection with the connection matching member 735 through the external thread of the pushing mechanism 73, and the implant 500 may be reliably fixed at the distal end of the hollow pushing member 73. After the implant 500 is pushed to a corresponding position of the bronchus, the connection member 57 of the implant 500 is screwed out of and separated from the connection matching member 735 of the hollow pushing member 73 by twisting the control handle 733 of the hollow pushing member 73. The connection member 57 and the connection matching member 735 may be connected through other detachably fixed connection components, such as magnetic connection devices, elastic buckles and ropes, which are disposed on the implant 500 and the hollow pushing member 103 respectively, to realize the detachable connection.

The assembly steps of the elastic implant 500 and the core wire 71 as well as the hollow pushing member 731 are as follows; first, connecting the elastic implant 500 with the connection matching member 735 at the distal end of the hollow pushing member 731 through the threads to communicate the hollow pushing member 731 with an inner channel of the elastic; implant 500; and then pushing the core wire 71 into the elastic implant 500 along a channel of the hollow pushing member 731 to restrict the elastic implant 500, which is normally curled in a natural state, into a tube in an approximately straight line type delivery state.

Referring to FIG. 15 to FIG. 18, an implant 500 equipped with the core wire 73 and the hollow pushing member 731 is delivered into the bronchus 1504 of a lung 1503 through a working channel 1502 of a bronchoscope 1501. With the assistance of X-rays, the implant 500 is pushed to an expected position by using the hollow pushing member 731, and then the core wire 71 is withdrawn. During withdrawal of the core wire 71, the implant 500 automatically recovers its natural shape as shown in FIG. 17 from the straight line type delivery state restricted by the core wire 71; and in this recovery process, the pulmonary emphysema region may be squeezed and pulled, and a relatively healthy lung tissue therearound may better exert a respiration physiological function, thereby achieving a lung volume reduction effect. The threaded connection between the connection matching member 735 at the distal end of the hollow pushing member 731 and the connection member 57 of the elastic implant 500 is released by rotating the handle 733, thereby releasing the implant 500.

Figure 19:
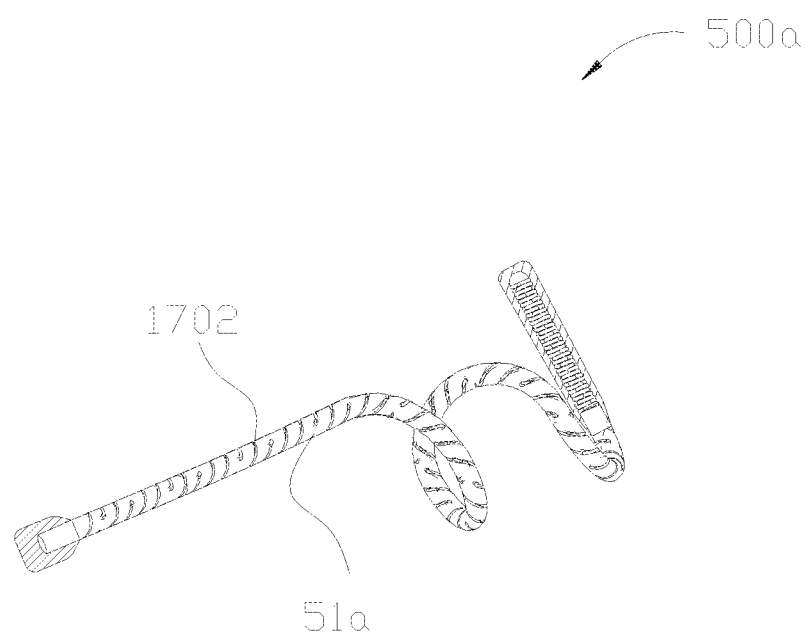
FIG. 19 is a schematic diagram of an implant provided by another embodiment of the present disclosure.
Figure 20:
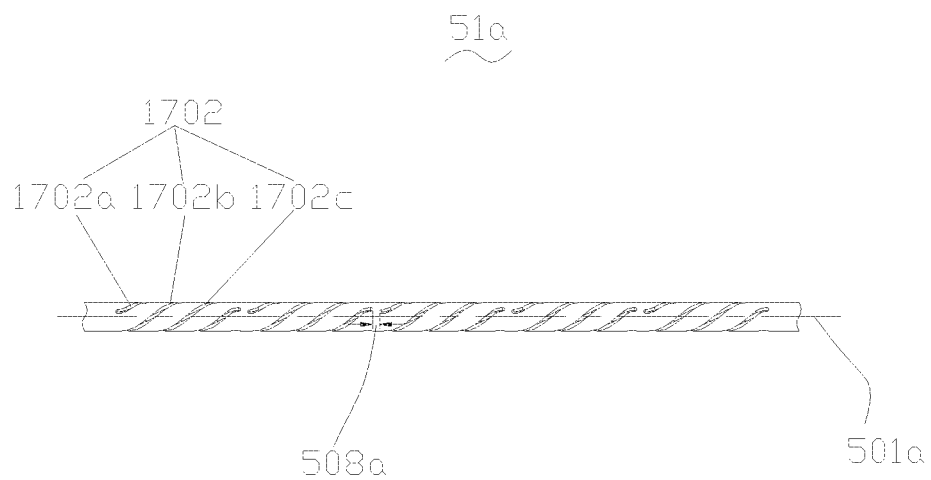
FIG. 20 is a schematic diagram of an elastic deformation section of the implant in FIG. 19.
Figure 21:
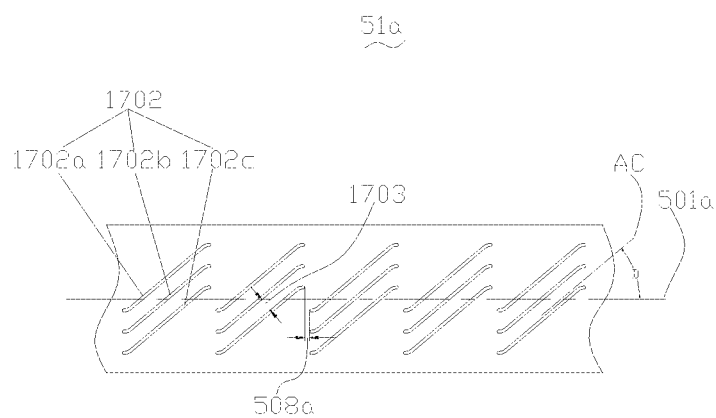
FIG. 21 is a schematic diagram of the elastic deformation section, which is split and unfolded along its lengthwise direction, in FIG. 20.

With reference to FIG. 19, an elastic implant 500a provided by another embodiment of the present disclosure is substantially the same as an implant 500, and what is different is that an elastic deformation section 51a of the implant 500a is different from the elastic deformation section 51 of the implant 500. To be more specific, referring to FIG. 20 and FIG. 21, the elastic deformation section 51a is provided with multiple groove groups 1702. After the elastic deformation section 51a is split along an axial direction and then flattened, it can be seen that each groove group 1702 includes three grooves 1702a, 1702b and 1702c which are arrayed in a circumferential direction of the elastic deformation section 51a, and are parallel to one another, and two ends of the three grooves are aligned with each other in the circumferential direction; and a certain gap 1703 is provided between every two adjacent grooves in each groove group 1702, and a gap 508a is provided between every two adjacent groove groups 1702. Each groove is of a thin structure, and the extending direction AC of the multiple grooves and the axial line 501a of the elastic deformation section 51a form a certain included angle D. The bending resistance of the entire elastic deformation section 51a may be adjusted to meet the implantation requirements by adjusting the number of the grooves and the gap 1703 in each groove group 1702, and the degree size of the included angle D between the extending direction AC of the grooves and the axial line 501a of the elastic deformation section 51a, and the gap 508a between every two adjacent groove groups 1702. In other embodiments, there may be two to six grooves in each groove group 1702, the gap 1703 between every two adjacent grooves in each groove group 1702 may be 0.05 to 1 mm, the included angle D may be 10 to 85 degrees, and the gap 508a between every two adjacent groups may be 0.1 to 1.0 mm. The outer diameter of the elastic deformation section 51a is about 1.0 to 2.0 mm, and the wall thickness is 0.05 to 0.3 mm.

Figure 22:
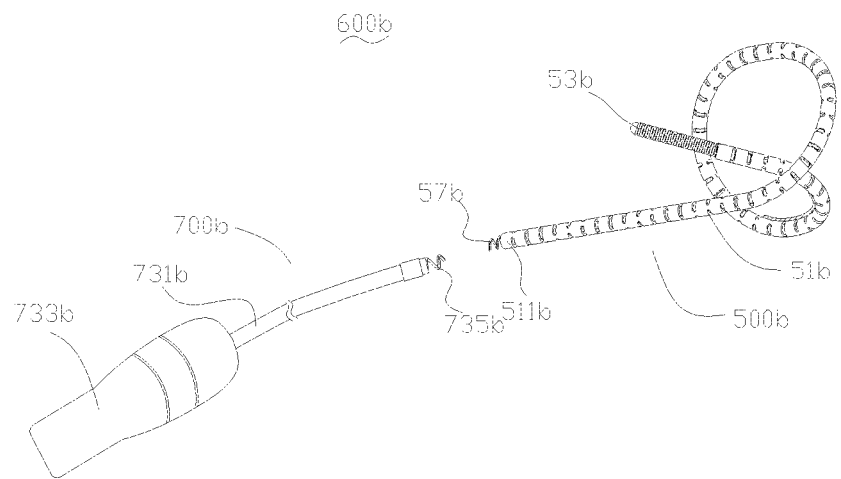
FIG. 22 is a schematic diagram of a lung volume reduction device provided by another embodiment of the present disclosure.

Referring to FIG. 22, a lung volume reduction device 600b provided by another embodiment of the present disclosure includes an implant 500b and a delivery device 700b.

Figure 23:
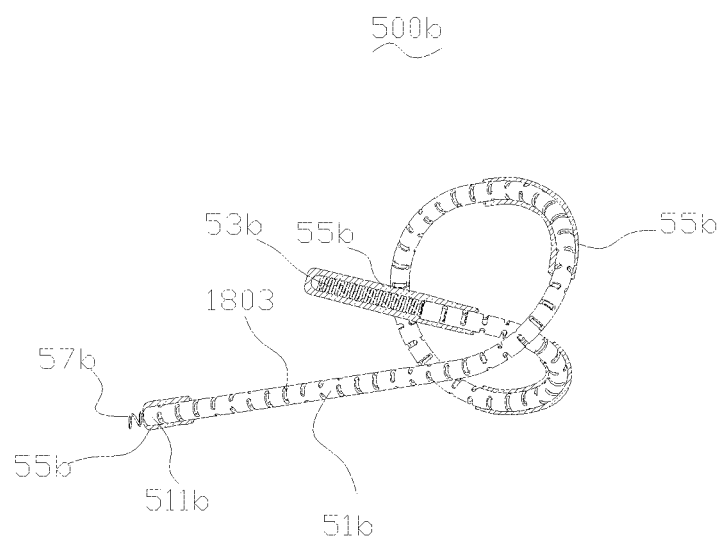
FIG. 23 is a schematic diagram of an implant of the lung volume reduction device in FIG. 22.
Figure 24:
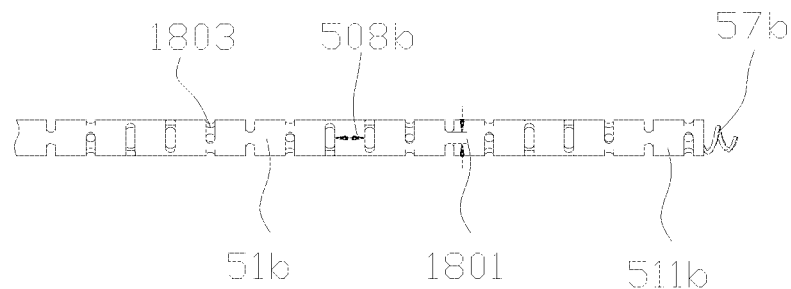
FIG. 24 is a schematic diagram of the proximal end of the implant in FIG. 23.
Figure 25:
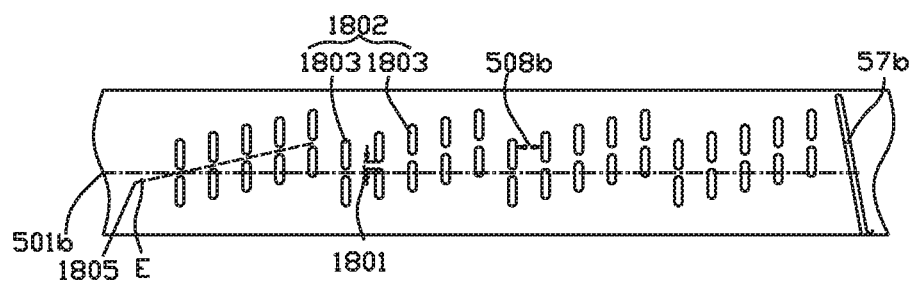
FIG. 25 is a schematic diagram of the proximal end, which is split and unfolded along lengthwise direction, of the implant in FIG. 23.

Referring together to FIG. 23 to FIG. 25, the tail end of the proximal end 511b of an elastic deformation section 51b of the implant 500b has a connection member 57b having a length of 0.5 to 2 mm. The elastic deformation section 51b includes multiple groove clusters 1802 which are arrayed in an axial direction of the elastic deformation section 51b in a spaced-apart manner. Each groove cluster 1802 consists of five elliptical groove groups 1803 which are disposed side by side and are arrayed in a stair-stepping manner. Each groove group 1803 in this embodiment consists of two side-by-side grooves 1803a and 1803b; a certain gap 1801 is reserved between the two grooves in each groove group 1803; and the long axis of each groove is perpendicular to the axial line of the elastic deformation section 51b. The extending direction 1805 of the arrangement of every two groups in each groove cluster 1802 and the axial line 501b of the elastic deformation section 51b form a certain included angle E which may be 60 to 90 degrees. A gap 508b of about 0.3 to 5 mm is formed between every two adjacent groove groups 1803 in each groove cluster 1802. The groove groups 1803 arrayed in the stair-stepping manner contribute to bending the elastic deformation section 51b into a specific shape. A portion having a length of about 0.5 to 5 mm at the proximal end 511b of the elastic deformation section 51b is cut into a threaded trench serving as a connection member 57b. A cut nickel-titanium tube is bent by a die into a shape as shown in FIG. 23, and then is subjected to thermal treatment modeling, thereby forming the elastic deformation section 51b of the elastic implant 500b. The bent portion of the elastic implant 500b and the outer surfaces, which have a length of about 1 to 10 mm, at the proximal ends 511b of the flexible guide section 53b and the elastic deformation section 51b, are wrapped by an elastic film 55b which has a thickness of 0.1 to 0.5 mm. In addition, the lumen of the elastic implant 500b is kept unblocked. In this implementation mode, the outer diameter of the implant 500b is 1.2 to 2.5 mm, and the wall thickness is 0.1 to 0.4 mm.

With reference to FIG. 22 again, a threaded connection matching member 735b that is matched with the connection member 75b is welded at the distal end of a hollow pushing member 731b of the delivery device 700b. During assembly, the threaded connection matching member 735b may be threadably connected with the connection member 57b of the elastic implant 500b; and when it is necessary to release the elastic implant 500b, the connection matching member 735b may be separated from the connection member 57b by rotating a handle 733b connected with the proximal end of the hollow pushing member 731b, thereby achieving the objective of releasing the elastic implant 500b.

Figure 26:
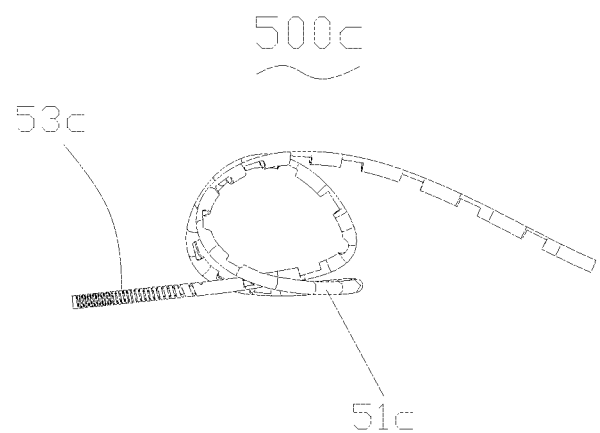
FIG. 26 is a schematic diagram of an implant provided by another embodiment of the present disclosure.
Figure 27:
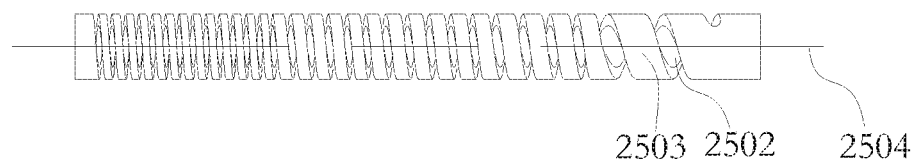
FIG. 27 is a schematic diagram of a flexible guide section of the implant in FIG. 26.
Figure 28:
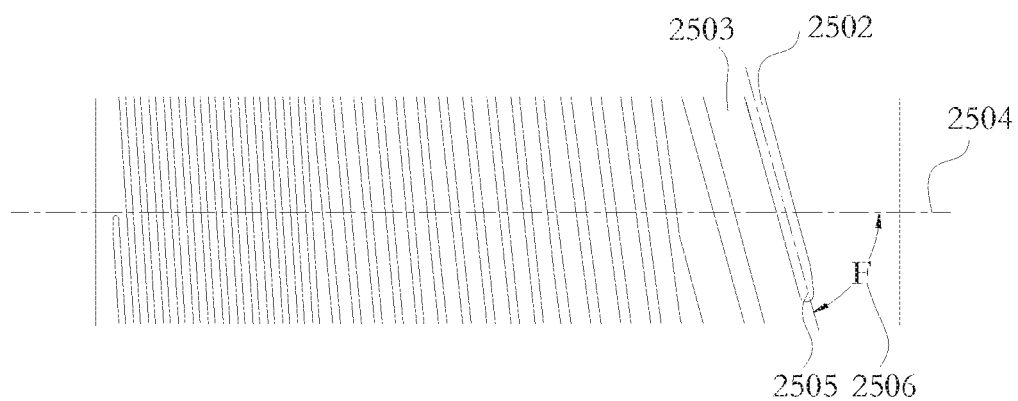
FIG. 28 is a schematic diagram of the flexible guide section, which is split and unfolded along its lengthwise direction, in FIG. 27.

With reference to FIG. 26, the proximal end of a flexible guide section 53c of an implant 500c provided by another embodiment of the present disclosure is connected with an elastic deformation section 51c via macromolecular heat-shrink tube or film wrapping, glue adhesion, laser welding, soldering and the like. With reference to the embodiment shown in FIG. 27 and FIG. 28, the flexible guide section 53c is a tubular body, which is cut from a nickel-titanium tube through laser and has continuous spiral grooves, and under the action of the same external force, its bending resistance is gradually enhanced from the distal end to the proximal end (that is to say, under the action of the same external force, its deformability is gradually lowered from the distal end to the proximal end), so as to achieve a better guide effect on the elastic implant 500c. It should be understood that as the flexible guide section 53c is a tubular body having multiple continuous spiral grooves, its bending resistance may vary with a change in the gap between every two adjacent grooves. A person skilled in the art could set the gap between every two adjacent grooves according to an desired actual requirement to achieve an objective that the bending resistance of the flexible guide section 53c is lower than that of the elastic deformation section 51.

The flexible guide section 53c includes the continuous spiral grooves 2502. On an unfolded plane formed by splitting the flexible guide section 53c along its axial direction, from the distal end to the proximal end of the flexible guide section 53c, the gap between every two adjacent grooves 2502 is gradually increased as well to achieve the objective of gradually enhancing the bending resistance of the flexible guide section 53c from the distal end to the proximal end.

It should be understood that on the unfolded plane formed by splitting the flexible guide section 53c along its axial direction, from the distal end to the proximal end of the flexible guide section 53c, when an included angle 2506 between the extending direction 2505 of the grooves 2502 of the flexible guide section 53c and the axial direction 2504 of the flexible guide section 53c is unchanged, and the widths of the grooves of the flexible guide section 53c in the axial direction 2504 of the flexible guide section 53c are gradually decreased, the gap between every two adjacent grooves 2502 is gradually increased as well, and the objective of gradually enhancing the bending resistance of the flexible guide section 53c from the distal end to the proximal end may be also achieved.

It should be understood that on the unfolded plane formed by splitting the flexible guide section 53c along its axial direction, from the distal end to the proximal end of the flexible guide section 53c, when the widths of the grooves of the flexible guide section 53c in the axial direction 2504 of the flexible guide section 53c are unchanged, and the included acute angle between the extending direction 2505 of the grooves of the flexible guide section 53c and the axial direction 2504 of the flexible guide section 53c is gradually enlarged, the gap between every two adjacent grooves 2502 is gradually increased as well, and the objective of gradually enhancing the bending resistance of the flexible guide section 53c from the distal end to the proximal end may be also achieved.

Figure 29:
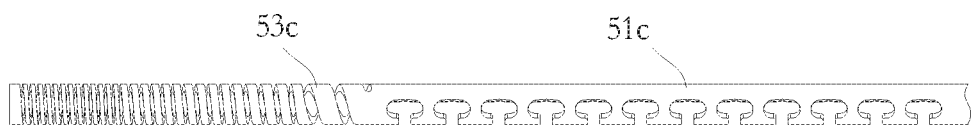
FIG. 29 is a schematic diagram of an elastic deformation section and the flexible guide section which are integrally formed.

A person skilled in the art may further understand that the components of this embodiment can be formed in an integral manner. Features of the elastic deformation section 51c and the flexible guide section 53c which are cut from the same nickel titanium tube through laser are as shown in FIG. 29, and the problems of low connection strength and the like which are caused by using a connection mode may be effectively avoided.

The above descriptions are made to the embodiments of the present disclosure in combination of drawings, but not intended to limit the present disclosure by the above-mentioned specific implementation modes which are merely schematic, but not restrictive. An ordinary person skilled in the art can also make many implementation modes without departing from the purpose of the present disclosure and the scope claimed by claims under an enlightenment of the present disclosure, and these implementation modes shall all fall within the protection of the present disclosure.

The invention claimed is:
1. In combination:
a lung volume reduction elastic implant, wherein the implant is tubular having a lumen, and has an open proximal end; the implant further comprising an elastic deformation section having a distal end and a lumen, and a flexible guide section connected with the distal end of the elastic deformation section; the elastic deformation section has a shape memory characteristic and has a plurality of grooves formed in a spaced-apart manner along its lengthwise direction; wherein each groove communicates with the lumen of the elastic deformation section; and wherein the flexible guide section is more flexible than the elastic deformation section; and
a core wire extending through the lumen of the implant; wherein the elastic deformation section has a proximal end, the combination further including: a pushing mechanism having a lumen and a distal end that is removably connected with the proximal end of the elastic deformation section, wherein the core wire extends through the lumen of the pushing mechanism.
2. The combination according to claim 1, wherein each groove has an incision direction and the elastic deformation section has a lengthwise direction, characterized in that an included angle between the incision direction of each groove and the lengthwise direction of the elastic deformation section ranges from 10 to 90 degrees.

3. The combination according to claim 2, wherein each of the elastic deformation section and the flexible guide section has an outer wall, further comprising an elastic film that at least wraps around the outer wall of the elastic deformation section and the flexible guide section.

4. The combination according to claim 3, wherein the grooves are further filled with the elastic film.

5. The combination according to claim 2, wherein the elastic deformation section also has a proximal end, characterized in that the elastic deformation section is made of a conical nickel-titanium tube having an outer diameter that gradually increases from the distal end to the proximal end, and a gap of 0.05 mm to 0.5 mm is formed between every two adjacent grooves of the elastic deformation section.

6. The combination according to claim 1, wherein the flexible guide section has a distal end and a proximal end, characterized in that the bending resistance of the flexible guide section is gradually enhanced from its distal end to its proximal end.

7. The combination according to claim 6, wherein the flexible guide section comprises a main body portion having a spring on the outer wall, the main body portion having an outer diameter, a distal end and a proximal end; wherein the proximal end of the main body portion is connected with the elastic deformation section; and the outer diameter of the main body portion is gradually increased from the distal end to the proximal end of the main body portion.

8. The combination according to claim 6, wherein the flexible guide section comprises a tubular body which is cut from a nickel-titanium tube and has continuous spiral grooves.

9. The combination according to claim 1, wherein the distal end of the flexible guide section has an axial line, and the distal end of the elastic deformation section also has an axial line, wherein an included angle is provided between the axial line of the distal end of the flexible guide section and the axial line of the distal end of the elastic deformation section, and the included angle ranges from 5 to 60 degrees.

10. A lung volume reduction elastic implant, wherein the implant is tubular having a lumen, and has an open proximal end, the implant further comprising:
an elastic deformation section having a distal end and a lumen, the elastic deformation section having a shape memory characteristic and a plurality of grooves formed in a spaced-apart manner along its lengthwise direction, and each groove of the elastic deformation section communicates with the lumen of the elastic deformation section;
a flexible guide section connected with the distal end of the elastic deformation section, the flexible guide section comprising a tubular body which is cut from a nickel-titanium tube and has continuous spiral grooves;
wherein the flexible guide section is more flexible than the elastic deformation section;
wherein the flexible guide section has a distal end and a proximal end, and a bending resistance which is gradually enhanced from its distal end to its proximal end; and
wherein a gap is provided between every two adjacent grooves of the flexible guide section, characterized in that the gap between every two adjacent grooves of the flexible guide section along the axial direction of the flexible guide section is gradually increased from the distal end to the proximal end of the flexible guide section.

11. The lung volume reduction elastic implant according to claim 10, wherein each groove of the flexible guide section has a width and an extending direction, the flexible guide section has an axial direction, and an included angle is provided between the extending direction of the grooves of the flexible guide section and the axial direction of the flexible guide section, wherein from the distal end to the proximal end of the flexible guide section, the included angle between the extending direction of the grooves of the flexible guide section and the axial direction of the flexible guide section is unchanged, and the widths of the grooves of the flexible guide section in the axial direction of the flexible guide section are gradually decreased.

12. The lung volume reduction elastic implant according to claim 10, wherein each groove of the flexible guide section has a width and an extending direction, the flexible guide section has an axial direction, and an included acute angle is provided between the extending direction of the grooves of the flexible guide section and the axial direction of the flexible guide section, wherein from the distal end to the proximal end of the flexible guide section, the widths of the grooves of the flexible guide section in the axial direction of the flexible guide section are unchanged, and the included acute angle between the extending direction of the grooves of the flexible guide section and the axial direction of the flexible guide section is gradually decreased.

13. A lung volume reduction elastic implant, wherein the implant is tubular having a lumen, and has an open proximal end, the implant further comprising:
an elastic deformation section having a distal end and a lumen, the elastic deformation section having a shape memory characteristic and a plurality of grooves formed in a spaced-apart manner along its lengthwise direction, and each groove of the elastic deformation section communicates with the lumen of the elastic deformation section;
a flexible guide section connected with the distal end of the elastic deformation section, the flexible guide section comprising a tubular body which has continuous spiral grooves;
wherein a gap is provided between every two adjacent grooves of the flexible guide section, characterized in that the gap between every two adjacent grooves of the flexible guide section along the axial direction of the flexible guide section is gradually increased from the distal end to the proximal end of the flexible guide section;
wherein the flexible guide section has a distal end and a proximal end, and a bending resistance which is gradually enhanced from its distal end to its proximal end.

14. The lung volume reduction elastic implant according to claim 13, wherein the flexible guide section is more flexible than the elastic deformation section.

15. The lung volume reduction elastic implant according to claim 14, wherein the flexible guide section has a distal end and a proximal end, and a bending resistance which is gradually enhanced from its distal end to its proximal end.

16. The lung volume reduction elastic implant according to claim 13, wherein each groove has an incision direction and the elastic deformation section has a lengthwise direction, characterized in that an included angle between the incision direction of each groove and the lengthwise direction of the elastic deformation section ranges from 10 to 90 degrees.

* * * * *